United States Patent [19]

Sanderson et al.

[11] Patent Number: 4,801,755

[45] Date of Patent: Jan. 31, 1989

[54] ISOBUTANE OXIDATION IN THE PRESENCE OF A SOLUBLE PROPYLENE GLYCOL/VANADIUM CATALYST

[75] Inventors: John R. Sanderson, Leander; Edward T. Marquis, Austin, both of Tex.

[73] Assignee: Texaco Inc., White Plains, N.Y.

[21] Appl. No.: 125,964

[22] Filed: Nov. 27, 1987

[51] Int. Cl.$^4$ ............................................. C07C 179/02
[52] U.S. Cl. ..................... 568/571; 568/575; 568/910; 568/910.5; 502/171
[58] Field of Search ............ 568/571, 575, 910, 910.5; 502/171

[56] References Cited

U.S. PATENT DOCUMENTS

| | | | |
|---|---|---|---|
| 2,265,948 | 12/1941 | Loder | 560/241 |
| 2,780,654 | 2/1957 | Robertson et al. | 568/860 |
| 2,845,461 | 7/1958 | Winkler et al. | 568/571 |
| 3,474,151 | 10/1969 | Grane | 568/913 |
| 3,825,605 | 7/1974 | Johnston | 568/910 |
| 3,832,149 | 8/1974 | Kozlowski et al. | 568/910 |
| 3,974,228 | 8/1976 | Barone | 568/571 |
| 4,028,423 | 6/1977 | Brownstein et al. | 568/570 |
| 4,296,262 | 10/1981 | Grane et al. | 568/910 |
| 4,296,263 | 10/1981 | Worrell | 568/910 |
| 4,328,365 | 5/1982 | Slinkard et al. | 562/512.2 |
| 4,569,925 | 2/1986 | Yang et al. | 502/209 |
| 4,722,919 | 2/1988 | Marquis et al. | 562/171 |

*Primary Examiner*—Bruce D. Grey
*Attorney, Agent, or Firm*—Jack H. Park; Kenneth R. Priem

[57] ABSTRACT

The oxidation of isobutane in the presence of a novel, soluble propylene glycol/vanadium catalyst is disclosed. Tertiary-butyl alcohol, tertiary-butyl hydroperoxide, and acetone are produced. A significant increase in isobutane conversion is obtained without a large decrease in selectivity to tertiary-butyl alcohol and tertiary-butyl hydroperoxide using a small amount of catalyst. Tertiary-butyl alcohol is useful as a gasoline additive and tertiary-butyl hydroperoxide is used for the production of propylene oxide. Acetone has a variety of uses as well.

4 Claims, No Drawings

ISOBUTANE OXIDATION IN THE PRESENCE OF A SOLUBLE PROPYLENE GLYCOL/VANADIUM CATALYST

BACKGROUND OF THE INVENTION

1. Field of the Invention

This invention relates to the oxidation of isobutane to tertiary-butyl alcohol and tertiary-butyl hydroperoxide by catalytic means.

2. Related Application

This application is related to U.S. Pat. No. 4,722,919. This application concerns the preparation of the vanadium/propylene glycol complex which is used as a catalyst herein.

Also, related application Ser. No. 125,965, filed of even date. That application concerns the oxidation of isobutane with an iron complex catalyst.

3. Description of Related Publications

U.S. Pat. No. 4,328,365 discloses a process for oxidizing lower aliphatic hydrocarbons using a vanadium catalyst.

U.S. Pat. No. 4,569,925 discloses a process for oxidizing aliphatic hydrocarbons using a vanadium catalyst.

Loder, U.S. Pat. No. 2,265,948 employs acetic acid as the solvent for oxidizing isobutane to TBA.

Robertson et al, U.S. Pat. No. 2,780,654 employs benzene as a solvent in oxidizing a mixture of isobutane and isobutene to a mixture of TBA and isobutylene glycol.

Winkler et al, U.S. Pat. No. 2,845,461 oxidizes liquid isobutane in the absence of catalyst to prepare a mixture of TBA and tertiary butyl hydroperoxide (TBHP).

Grane, U.S. Pat. No. 3,474,151 heats TBA at 375°–475° F. for a few minutes, whereby traces of TBHP are thermally decomposed to provide a TBA suitable for blending into gasoline.

Johnston, U.S. Pat. No. 3,825,605 oxidizes isobutane to TBA using a solid catalyst comprising molybdenum oxide, and minor amounts of two other metals (from a group comprising cobalt, iron, or chromium).

Kozlowski et al, U.S. Pat. No. 3,832,149 prepares a motor fuel consisting of a mixture of alkylate and an oxylate prepared by hydrogenating the oxidate derived from oxidizing isobutane.

Barone, U.S. Pat. No. 3,974,228, employs a buffer such as lanthanum carbonate in oxidizing isobutane to TBHP.

Browntein et al, U.S. Pat. No. 4,028,423 oxidizes isobutane to TBA and TBHP using a copper polyphthalocyanine catalyst activated with an aromatic amine.

U.S. Pat. No. 4,296,263 describes the oxidation of isobutane/n-butane mixtures in the presence of chromium, copper, nickel, manganese, molbydenum, etc.

U.S. Pat. No. 4,296,262 describes the oxidation of isobutane in the presence of molybdenum.

The present invention to be described below is a method of preparing tertiary-butyl alcohol, as well as tertiary-butyl hydroperoxide, by the oxidation of isobutane in the presence of a novel catalyst.

SUMMARY OF THE INVENTION

In accordance with the present invention, isobutane is oxidized with an oxygen-containing material to produce a liquid effluent comprising both tertiary butyl alcohol (TBA) and tertiary butyl hydroperoxide (TBHP) in the presence of an effective amount of a soluble propylene glycol/vanadium catalyst.

DESCRIPTION OF THE PREFERRED EMBODIMENTS

The soluble propylene glycol/vanadium catalyst is described in U.S. Pat. No. 4,722,919. The entire application is incorporated by reference. Especially descriptive is page 3 beginning at line 25 and continuing throughout the entire application. The particular catalyst used in the examples following herein are from Example 9 in U.S. Pat. No. 4,722,919.

The useful vanadium compounds are preferably vanadium compounds which contain ammonium ligands as well as oxygen. Such materials include ammonium metavanadate, and hydrates forms thereof, vanadium triisopropoxide oxide, vanadium tri-n-propoxide oxide, vanadyl acetylacetonate, vanadium pentoxide, etc.

Propylene glycol is the other co-reactant used to make suitable vanadium complexes.

For the propylene glycol/vanadium compound system, the preferred reactant ratios are 7:1 to 20:1 expressed in terms of moles of propylene glycol to gram atoms of vanadium in the vanadium compound. A preferred range of moles of propylene glycol to gram atoms of vanadium is 8:1 to 16:1. To provide the best complex in terms of vanadium content, ease of processing and stability upon standing, the proportion of water remaining in the complex should be in the range of 0.1 to 2.0 wt %. The reaction temperature to make the inventive complexes should be between about 80° and 130° C., preferably 90° to 120° C, and the pressure should be atmospheric. High reaction temperatures, on the order of 165° to 180° C. with vanadium complex preparations lead to sharply reduced vanadium contents and large formation of solids. With the techniques described herein, liquid complexes with vanadium contents of 2 to 9% are possible. Typically, these vanadium contents are 3 to 6% or of the narrower range of 3 to 4%. Such high levels of vanadium in stable liquid complexes are much better than those otherwise attainable. Generally, no filtration is required for the best complexes of this invention. In a preferred embodiment, the reactants are heated to about 90° to 120° C. for about one hour, cooled and then subjected to a vacuum of 10 to 100 mm Hg to remove water and propylene glycol, for 30 to 60 minutes. The temperature of the pot should rise to about 90° to 110° C. during the stripping and the pressure should be adjusted to achieve and maintain this temperature. Sufficient overhead is removed so that the complex bottoms amount to about 70 to 95 wt % of the charge and the water content of the catalyst is preferably in the 0.1 to 2 wt % range. Generally, the water content of the final complex should be between about 0.1 and 3.0 wt %.

It should be noted that these complexes are surprisingly made very simply and require no corrosive acids, amines, etc. They are made at mild temperatures and with short reaction times. The complexes require very little or no filtration and appear to remain stable indefinitely. In addition, the processing costs and reactant costs to make these complexes are minimal.

The complexes and method of this invention are more particularly illustrated by the following examples which should not be construed as limiting the invention in any way.

Since these vanadium/propylene glycol complexes titrate as acids, even though they have no free acidic groups, they are useful as acid catalyst substitutes.

The oxidation of isobutane with the catalyst described above is typically conducted by reacting an isobutane with an oxygen in the presence of the catalyst and a solvent which can be tertiary butyl alcohol (TBA). The products are principally tertiary butyl alcohol (TBA), tertiary butyl hydroperoxide (TBHP) and acetone.

Pure oxygen can be used. Also, air and mixtures of oxygen with inert materials are examples of useful materials to oxidize the isobutane. One skilled in the art would be aware of various useful oxygen-containing materials.

Preferably, the catalyst concentration is from about 5 to 5000 ppm based on the combination of the hydrocarbon, the alcohol, and the organic hydroperoxide. Further, the reaction should be conducted at a temperature in the range of about 125° C. to 185° C., preferably about 134° C to 165° C. and especially in the range of about 145° C to 155° C. The pressure should be maintained within the range from about 300 to 1500 psig, preferrably about 400 to 800 at residence time of from about 0.50 to 10.0 hours, preferably from 2 to 6 hours. By method of this invention a significant increase in isobutane conversion is obtained without a large decrease in selectivity to TBA and TBHP using a very small amount of catalyst. Of course, higher conversion of isobutane will yield more TBA and lower conversion will yield more TBHP. The parameters above can be easily controlled by skilled art workers to achieve the results desired.

EXAMPLES

A mixture of TBHP and TBA equivalent to 5-6% conversion [along with the catalyst (if any) dissolved in a small amount of TBA] was charged to the reactor through a small vent hole near the top of the reactor. The autoclave was sealed and enough isobutane pressured in to give a pressure of 600 psi at the reaction temperature. The autoclave was then heated to the desired temperature and oxygen added in approximately 1 gram increments until a pressure 150-200 psi over autogeneous was reached. Oxygen was then added only after the pressure had dropped 50 psi. The reaction was continued for the desired length of time. The mixture was cooled as rapidly as possible to ambient temperature and the reactor contents pressured out into a tared stainless-steel bomb. The products were determined by GC analysis and the results are shown in the following table:

TABLE

Isobutane Peroxidation in a 300 cc Stainless Steel Autoclave[a]

| Note-book no. | V Catalyst[b] grams) | Time (hr) | Temp (°C.) | IB[c] Conv. % | Selectivity, %[c] | | |
|---|---|---|---|---|---|---|---|
| | | | | | TBHP | TBA | Acetone |
| 5997-5 | 0.011 | 4.0 | 145 | 58.45 | 3.86 | 80.67 | 15.38 |
| 5997-36 | 0.012 | 2.0 | 145 | 26.86 | 19.79 | 73.69 | 6.39 |
| 5997-6 | 0.021 | 2.0 | 145 | 32.32 | 15.16 | 75.05 | 9.67 |
| 5997-7 | 0.043 | 2.0 | 145 | 29.51 | 10.57 | 80.00 | 9.32 |
| 5987-79 | 0 | 4.0 | 145 | 29.88 | 53.03 | 44.16 | 2.56 |
| 5987-60-5 | 0 | 7.0 | 145 | 60.69 | 45.17 | 50.43 | 4.29 |
| 5997-39 | 0.024 | 4.0 | 135 | 35.54 | 20.14 | 74.51 | 5.26 |
| 5997-45 | 0.027 | 2.0 | 125 | 15.81 | 26.16 | 29.26 | 4.48 |
| 5829-6 | 0 | 4.0 | 135 | 17.4 | 66.3 | 31.9 | 1.30 |
| 5829-23 | 0 | 2.0 | 135 | 6.79 | 70.2 | 28.4 | 0.84 |
| 5997-47 | 0.020 | 4.0 | 125 | 17.96 | 36.80 | 60.84 | 1.79 |
| 5829-44 | 0 | 4.0 | 125 | 7.16 | 77.8 | 21.7 | 0.24 |

[a] = About 100 g TBHP + TBA + IB charged.
[b] = A soluble PG/V catalyst containing 3.98% V [notebook no. 5940-63-2]
[c] = IB = isobutane. TBHP = tert-butyl hydroperoxide. TBA = tert-butyl alcohol

We claim:

1. A method for oxidizing isobutane with an oxygen-containing material in the presence of an effective amount of a soluble propylene glycol/vanadium catalyst.

2. The method of claim 1 wherein the catalyst concentration is about 5 to 5000 ppm.

3. The method as in claim 1 wherein the reaction is conducted at a temperature in the range of about 125° C. to 185° C. and at a pressure in the range from about 300 to 1500 psig.

4. The method for oxidizing isobutane comprising reacting isobutane with an oxygen-containing material in the presence of a soluble propylene glycol/vanadium catalyst wherein the catalyst concentration is about 5 to 5000 ppm, the temperature is in the range from about 125° C. to 185° C. and the pressure is in the range from about 300 to 1500 psig.

* * * * *